United States Patent [19]
Reo et al.

[11] Patent Number: 5,429,825
[45] Date of Patent: Jul. 4, 1995

[54] ROTOMELT GRANULATION

[75] Inventors: Joseph P. Reo, Harleysville; Edward J. Roche, Paoli, both of Pa.

[73] Assignee: McNeil-PPC, Inc., Milltown, N.J.

[21] Appl. No.: 904,940

[22] Filed: Jun. 26, 1992

[51] Int. Cl.$^6$ .............................................. A61K 9/16
[52] U.S. Cl. .................................. 424/490; 424/499; 424/501; 424/502
[58] Field of Search ............... 424/490, 489, 499, 501, 424/502; 427/213

[56] References Cited

U.S. PATENT DOCUMENTS

| | | | |
|---|---|---|---|
| 4,505,953 | 5/1985 | Chen et al. | 427/212 |
| 4,871,549 | 10/1989 | Ueda et al. | 424/494 |
| 5,019,302 | 5/1991 | Sparks et al. | 264/8 |
| 5,028,433 | 7/1991 | Ishimaru et al. | 424/464 |
| 5,104,648 | 4/1992 | Denton et al. | 424/78.35 |
| 5,215,755 | 6/1993 | Roche et al. | 424/480 |

FOREIGN PATENT DOCUMENTS

| | | | |
|---|---|---|---|
| 0409254A1 | 1/1991 | European Pat. Off. | A61K 9/14 |
| 0452145A2 | 10/1991 | European Pat. Off. | A61K 9/14 |

OTHER PUBLICATIONS

Handbook of Pharmaceutical Excipients, Am. Pharm. Assn., Washn. D.C., pp. 234 and 236, (1986).

The Merck Index, 11th Ed., Merck & Co., Rahway, N.J., pp. 7635, (1989).

The United States Pharmacopeia, USP XXII, NF XVII, U.S. Pharmacopeial Convention, Inc., Rockville, Md., p. 200 (1990).

Jager et al., "Effect of Material Motion on Agglomeration in the Rotary Fluidized-Bed Granulator", *Drugs Made in Germany*, vol. XXV, pp. 61–65, 1982.

Y. Haramushi et al., "Study on Fluidized Melt-Granulation I. Examination of the Factors on the Granulation", *Yakugaku Zasshi*, vol. 111, No. 9, pp. 515–523 (1991).

*Primary Examiner*—Thurman K. Page
*Assistant Examiner*—Amy Hulina
*Attorney, Agent, or Firm*—Bernard F. Plantz

[57] ABSTRACT

A process for producing granules by rotomelt granulation comprising mixing at least one powdered pharmaceutically active material and a powdered excipient material within a zone wherein both powdered materials are maintained in a fluidized state by a rising stream of gas in an apparatus having a rapidly rotating horizontal-disk located within a vertical vessel wherein said gas is at a temperature sufficient to cause at least one powdered material to at least partially melt thereby causing said powdered materials to aggregate and form granules.

14 Claims, 1 Drawing Sheet

ROTOMELT GRANULATION

FIELD OF INVENTION

This invention relates to a process for the production of spherical particles or granules. The granules produced by this process are particularly well suited for pharmaceutical uses.

BACKGROUND OF THE INVENTION

Greater than 90% of all therapeutic compounds are administered via the oral route, of which the tablet dosage form is by far the most popular. The quality of this solid oral dosage form is, as a general rule, primarily governed by the physical and chemical properties of the granulation from which the tablets are composed.

It is particularly important in the granulation process to be able to control the granules size distribution, shape and surface characteristics. These granule characteristics in turn affect the formulation design and manufacture of tablets and capsules as well as impacting the bioavailability of the active pharmaceutical components in the granules.

Many techniques are known for preparing granulations from powdered materials such as wet granulation, solvent granulation and melt granulation. All of these techniques involve the addition of an inactive binder to aggregate smaller particles into larger granules. For example, wet granulation and solvent granulation require the addition of a liquid binder which aggregates the active materials and excipients into granules. After granulation, the liquid generally must be removed by a separate drying step. Melt granulation is similar to wet granulation, but uses a low melting point solid material as a binder. The solid binder in melt granulation is melted and acts as a liquid binder thereby aggregating the powdered active material and excipients into granules. The binder thereby, is permanently incorporated into the granules when the granules cool.

Each of these granulation techniques has drawbacks. Wet granulation requires a liquid be added which requires tanks and handling equipments. Since the liquid used in wet granulation must subsequently be removed, a drying step is also needed which requires drying equipment and further complicates the manufacturing process. Additionally, wet granulation is not well suited to making granules which incorporate water absorbing disintegrants. Unless the wet granulation is very carefully controlled the water absorbing disintegrant will absorb the water as it is added to the granulation and result in a swollen mass being formed instead of discreet granules. To solve this problem and avoid the inactivation of water sensitive pharmaceuticals a solvent based granulation can be used. The solvent used in this granulation process is generally a volatile hydrocarbon or alcohol which can easily be removed from the granules after they are formed. Since water is not involved in this granulation process the problems with the incorporation of disintegrants and inactivation of pharmaceuticals is avoided. However, the use of highly volatile solvents present a new set of problems. The foremost problem with solvent granulation is the risk of explosion which can occur any time one is handling volatile solvents. Special precaution are necessary to avoid explosions and protect worker from exposure to these solvents.

Melt granulation on the other hand avoids the problems associated with adding liquids by incorporating a low melting solid binder. The low melting point binder must be heated to at least its softening point and melted during the granulation process. The heat necessary to soften or melt the binder is generally supplied by a high shear mixing device. Unfortunately, it is difficult to control the heat distribution generated by high shear mixing which may result in heat inactivation of some active materials. Another significant problem with melt granulation with high shear mixing is that the granules formed have a broad distribution of granule sizes and tend to be fragile. These characteristics make the granules difficult to handle in subsequent processing into tablets and capsules and significantly contribute to product waste.

Thus, it would be a significant advancement to the art if a new process for granulation could be developed.

SUMMARY OF THE INVENTION

Thus, it is an object of the present invention to provide a new granulation process.

It is another object of the present invention to provide a new granulation process in which water absorbent disintegrants may be easily incorporated.

It is a further object of the present invention to provide a new granulation process in which the process parameters may be easily controlled to provide a narrow distribution of granule sizes.

These and many other objects and advantages of the present invention will be apparent from the following detailed description, examples, claims and figures.

One embodiment of the present invention is a process for producing granules by rotomelt granulation comprising mixing at least one powdered pharmaceutically active material and a powdered excipient material with a higher melting point than said powdered pharmaceutically active material in a zone wherein both powdered materials are maintained in a fluidized state by a rising stream of gas in an apparatus having a rapidly rotating horizontal-disk located within a vertical vessel having a bottom surface and said rapidly rotating disk is located on the bottom surface of the vertical vessel wherein said gas is at a temperature sufficient to cause at least one powdered pharmaceutically active material to at least partially melt thereby causing said powdered materials to aggregate and form granules.

A further embodiment of the present invention is a process for producing granules by rotomelt granulation comprising mixing powdered binder material and a powdered pharmaceutically active material with a higher melting point than said powdered binder material in a zone wherein both powdered materials are maintained in a fluidized state by a rising stream of gas in an apparatus having a rapidly rotating horizontal-disk located within a vertical vessel having a bottom surface and said rapidly rotating disk is located on the bottom surface of the vertical vessel wherein said gas is at a temperature sufficient to cause the powdered binder material to at least partially melt thereby causing said powdered materials to aggregate and form granules.

BRIEF DESCRIPTION OF THE DRAWING

The accompanying drawing illustrates one apparatus suitable for use in the process of rotomelt granulation:

DETAILED DESCRIPTION OF THE INVENTION

Figure 1:
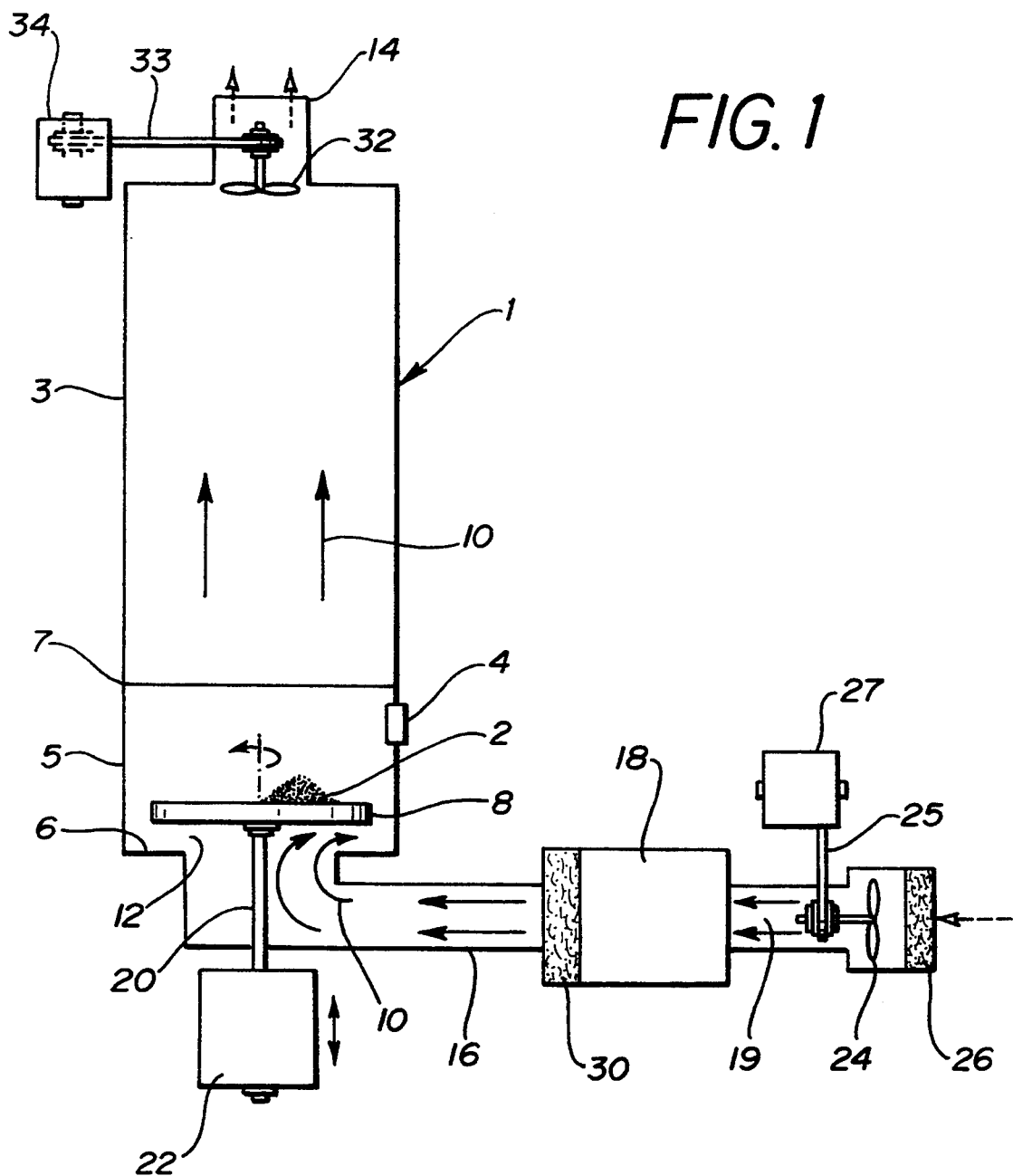
FIG. 1 is a diagrammatic view of a apparatus suitable for use in the process of rotomelt granulation.

The present invention provides a process for producing granules suitable for utilization in the formulation of pharmaceuticals. Granules with a particle size of from in the range of from about 150 μm to about 2000 μm and preferably in the range of from about 250 μm to about 1250 μm can easily be formed. The granules will also have a nearly spherical shape which will allow the granules to be evenly coated by conventional means such as Wurster apparatus or tangential coating apparatus. Coated granules produced by the present invention also improve the taste masking and controlled release properties of these granules. Granules produced by this process also have a narrow size distribution which reduces waste and makes subsequent processing of the granules into tablets and capsules easier. This process for producing the granules will be referred to as rotomelt granulation.

In rotomelt granulation, one of the feed powders must have a lower melting point than the other powder to serve as a binder. The feed powders are introduced into a vertical vessel with rotatable horizontal-disk located in the bottom of the vessel. The powder is maintained in fluidized state by at least one stream of filtered air being circulated from the bottom of the vertical vessel through one or more inlets. The rotatable horizontal disk is then rotated while the air supplied to fluidize the powder is maintained at a temperature sufficient to soften or melt the lower melting point powder. The temperature to which the binder must be heated to soften can be empirically determined by observing the formation of granules at various temperatures for various binders. It is presently believed that temperatures 3°-5° C. below the melting point or melting range provide sufficient softening to result in granule formation. The lower melting point powder then acts as a binding agent to promote the aggregation of powder particles into granules.

Suitable powders for use in rotomelt granulation should have a diameter size in the range of from about 5 μm to about 150 μm and preferably in the range of about 35 μm to about 80 μm. The powdered components should be active pharmaceutical compounds, pharmaceutically acceptable binders and excipients that are stable at elevated temperatures. The temperature which the components will be exposed to depends on the binder employed to aggregate the powders. Generally, the melting point of the binder will be above 30° C. and preferably below 100° C.

The powders used in the present invention can be formed into granules by at least two alternative granulation mechanisms. The first mechanism for granule formation utilizes a larger particulate binder and a smaller particulate powder. The temperature during the rotomelt granulation is then elevated only to the point where the external surface of the binder particles become tacky. As the second powdered material of a smaller size is contacted with the tacky surface it forms a microlayer on the surface of the binder particle. This granulation mechanism results in granules which have size distribution similar to the original binder particles employed. Alternatively, the rotomelt granulation may be conducted at a temperature at which the binder acts as a cement bridging the gaps between the unmelted particles (this is referred to as agglomeration). This mechanism results in the formation of granules where the components are intermingled. For each binder used the mechanism can be controlled primarily by the temperature at which the rotomelt granulation is preformed. Those skilled in the art will appreciate that the granules formed can be observed by electron microscopy to determine the type of granulation process occurring. If one particular type of granule is desired, the process conditions or starting materials can be varied to produce the desired granules.

In one embodiment of the present invention, the active pharmaceutical compound is melted to act as a binding agent in the rotomelt granulation process. In this embodiment of the invention the active pharmaceutical compound must be capable of being melted without decomposing or becoming inactive. Suitable active pharmaceutical compounds which may be melted to act as a binding agent include but are not limited to pharmaceutical compounds selected from the group consisting of gemfibrozil, guaifenesin, ibuprofen, isosorbide dinitrate, flurbiprofen and ketoprofen. The preferred active pharmaceutical compound is ibuprofen. In this embodiment of the invention ibuprofen will act as a binder when heated to above 68° C. and most preferably to a temperature in the range of from about 68° C. to about 76° C.

Suitable excipients for the present invention must be pharmaceutically acceptable excipients selected with a suitable thermal stability for the thermal exposure it will receive during the rotomelt granulation process. Excipients which may be added to the powdered active pharmaceutical compound include excipients selected from the group consisting of fillers, disintegrants, lubricants, glidants and antiadherents. Suitable fillers include but are not limited to calcium phosphate dibasic, tricalcium phosphate, calcium carbonate, starch (such as corn, maize, potato and rice starches), modified starches (such as carboxymethyl starch, etc.), microcrystalline cellulose, sucrose, dextrose, maltodextrins, lactose, and fructose. Suitable disintegrants include but are not limited to disintegrants provided in an effective amount selected from the group consisting of starch (such as corn, maize, waxy maize, potato and rice starches), derivative of starch (such as carboxymethyl starches, and sodium starch glycolate such as Explotab®), purified wood cellulose, cellulose derivatives (such as methyl cellulose, carboxymethyl cellulose, crosslinked carboxymethyl cellulose, low substituted hydroxypropyl cellulose, microcrystalline cellulose and combinations thereof such as sodium carboxymethyl cellulose and microcrystalline cellulose), alginic acid, guar gum, pectins, cation exchange resins, crosslinked homopolymers of vinylpyrrolidone (Polyplasdone® XL and XL10) and finely divided solids (such as magnesium silicates, aluminium silicates and colloidal silicon). Suitable lubricants include but are not limited to metal stearates (such as calcium, magnesium on zinc stearates), stearic acid, hydrogenated vegetable oils, talc, starch, light mineral oil, sodium benzoate, sodium chloride, sodium lauryl sulfate, magnesium lauryl sulfate, sodium stearyl fumarate, glyceryl behenate and polyethylene glycol (such as Carbowax 4000 and 6000). Suitable antiadherents include but are not limited to colloidal silicon dioxide.

The illustrative excipients listed above are known in the art and have been described in several books such as the *Handbook of Pharmaceutical Excipients*, published by the American Pharmaceutical Association (1988), and *Pharmaceutical Dosage Forms: Tablets*, Vol. 1-3, second edition, edited by Herbert A. Lieberman, Leon Lachman and Joseph B. Schwartz, published by Marcel Dekker (1989), which are hereby incorporated by reference. Further information on disintegrants is available from a variety of sources such as the article "A Comparative Evaluation of the Properties of Some Tablet Disintegrants" by D. Gissinger and A. Stamm published in Drug Development and Industrial Pharmacy, 6(5), 511-536 (1980) which is hereby incorporated by reference.

The amount of binder which is necessary to add to aggregate the particles into granules generally is in the range of from about 10 weight percent to about 80 weight percent and preferably is in the range of from 30 to 70 weight percent of the powdered materials in the rotomelt granulation the remaining weight percent to provide a total of 100 weight percent being one or more suitable powdered pharmaceutical actives. Optionally the rotomelt granulation may also contain from in the range of about 0 to about 60 weight percent of one or more powdered excipients and/or powdered dissolution enhancers wherein the total weight of all the powdered materials equals 100 weight percent. Dissolution enhancers are pharmaceutically acceptable alkali carbonates such as sodium carbonate, potassium carbonate and sodium bicarbonate which produce gas when contacted with stomach acids.

One suitable formulation of ingredients which may be made into granules would consist of from in the range of about 20 to about 80 weight percent powdered ibuprofen and preferably from in the range of about 30 to about 70 weight percent ibuprofen based on the total weight of the powder materials equalling 100 weight percent. The remaining weight percent of the powder material consist of excipients such as disintegrants and fillers including but not limited to disintegrants and fillers selected from the group consisting of corn starch, maize starch, waxy maize starch, potato starch, rice starch, carboxymethyl starches, sodium starch glycolate, purified wood cellulose, carboxy cellulose, carboxymethyl cellulose, crosslinked carboxymethyl cellulose, low substituted hydroxypropyl cellulose, microcrystalline cellulose, combinations of sodium carboxymethyl cellulose and microcrystalline cellulose, alginic acid, guar gum, pectins, cation exchange resins, crosslinked homopolymers of vinylpyrrolidone, magnesium silicates, aluminium silicates, colloidal silicon, sucrose, dextrose, maltodextrins, lactose, and fructose combination of two or more thereof.

Ibuprofen may also be formulated in a three component system which would consist of from in the range of from about 10 to about 60 weight percent ibuprofen, from in the range of from about 20 to about 40 weight percent of a powdered excipient such as a disintegrant or filler and from in the range of from about 20 to about 70 weight percent of a powdered dissolution enhancer wherein the total weight percent of all the powdered materials equals 100 weight percent.

In another embodiment of this invention a separate inactive powdered material is used as the binder. The binder used in this embodiment of the invention should be a pharmaceutically acceptable dry powder having a particle size in the range of from about 5 $\mu$m to about 150 $\mu$m and preferably in the range of from 35 $\mu$m to 80 $\mu$m. Suitable binders for rotomelt granulation are low melting point powdered binder selected from the group consisting of polyethylene glycol 4000, polyethylene glycol 6000, stearic acid, and low melting point waxes. Suitable low melting point waxes include but are not limited to glyceryl monostearate, hydrogenated tallow, myristyl alcohol, myristic acid, stearyl alcohol, substituted monoglycerides, substituted diglycerides, substituted triglycerides, white beeswax, carnauba wax, castor wax, japan wax, acetylate monoglycerides and combinations of two or more thereof. It is currently preferred that the binders used in the present invention generally have a melting point from about 30° C. to 100° C. and most preferably between 40° C. to 85° C.

Suitable pharmaceutically active materials for this embodiment of the invention should be thermally stable pharmaceuticals. For the purpose of this invention a pharmaceutical active will be generally suitable for use in this invention if it does not decompose or become inactive after by being exposed to a temperature of at least 30° C. for at least 20 minutes. The thermal stability required for a particular combination of materials depends on the temperature required to melt the binder employed. The following active pharmaceutical compounds are suitable for rotomelt granulation which include but are not limited to antihistamines including terfenadine, chlorpheniramine maleate, clemastine fumarate, carbinoxamine maleate, promethazine hydrochloride, and diphenhydramine; analgesics and antipyretics including aspirin, salicylamide, ethanzamide, acetaminophen and diclofenac sodium; bronchodilators including salts of dpseudoephedrine; antitussives and expectorants including dextromethorphan hydrobromide, dihydrocodeine phosphate, cloperastine hydrochloride, phenylpropanolamine hydrochloride, methylephedrine, potassium cresol sulfonate, morphine sulfate, codeine phosphate and belladonna alkaloids; antiulcers including pirenzepine, cimetidine, ranitidine and famotidine; drugs for circulatory organs including pindolol, propranonol, alprenolol, oxprenolol and diltiazem; antitumor agents including 5-fluorouracil; antibiotics including cephalexin and cefaclor; antibacterials including cinoxacin, enoxacin and ofloaxacin; and pharmaceutically acceptable salts thereof.

The amount of binder which is necessary to add to aggregate the particles into granules generally is in the range of from about 10 weight percent to about 80 weight percent and preferably is in the range of from 30 to 70 weight percent of the powdered materials in the rotomelt granulation the remaining weight percent to provide a total of 100 weight percent being a suitable pharmaceutical active. Optionally one or more of the excipients and/or dissolution enhancers already described may be employed with the binder and the pharmaceutical active. The excipient and/or dissolution enhancer may comprise from 0 weight percent to about 60 weight percent of the powdered materials wherein the total weight percent of the powdered materials equals 100 weight percent.

Presently it is preferred that the granules formed by the present invention will be small enough to pass through a 20 mesh U.S Standard screen and large enough to be retained on a 100 mesh U.S. Standard screen which is approximately a particle size in the range of from about 900 $\mu$m to about 200 $\mu$m. Most preferably the granules formed by the present invention will have a narrow size distribution such that at least 50 weight percent and preferably at least 75 weight percent will have a particle size that is within a 200 $\mu$m range of size, most preferably at least 50 weight percent of the granules will have a particle size within a 100 $\mu$m range of size. As is shown in Examples 2-4 this may readily be accomplished using the process of the present invention.

The granules formed by rotomelt granulation are particularly well suited for coating with taste masking coatings such a mixture of cellulose acetate, cellulose acetate butyrate and polyvinylpyrrolidone or hydroxypropyl cellulose and cellulose acetate phthalate alone or in combination with polyvinylpyrrolidone or hydroxypropyl cellulose. Suitable coating have also been described in patents such as U.S. Pat. No. 5,075,114 and U.S. Pat. No. 4,851,226 which are hereby incorporated by reference herein. Granules made by this process may be coated using conventional pan coating, Wurster coating or rotocoating methods.

Granules formed by this process are also suitable for mixing with pharmaceutically acceptable excipients and forming into chewable or swallowable tablets, pills or capsules.

The process and apparatus suitable for performing rotomelt granulation may be further understood by referring to FIG. 1 which illustrates diagrammatically a preferred apparatus for utilization in the rotomelt granulation process. In the rotomelt granulation process the powdered materials 2 are introduced into a vertical walled vessel 1, which is generally cylindrical in shape, by separating the lower section of the vessel 5 from the upper section or expansion chamber 3 of the vertical walled vessel at seam 7 or through an inlet means 4. In the lower section 5 of the vessel, the powdered material is contacted with a horizontally rotatable disk 8 located on and in the center of the bottom surface of the vertical walled vessel 6. The horizontally rotatable disk 8 is movably linked to shaft 20 which transmit torque to said rotatable disk 8. Said movable linkage allowing said rotatable disk to be displaced vertically as well as rotated in the horizontal plane. The shaft 20 is mechanically linked with a means for providing torque such as a variable speed motor 22. The shaft mechanically displaces the horizontal rotatable disk 8, upwards creating a path for the air 10, to enter the lower section of the vertical walled vessel 5 between the bottom surface of the vessel 6 and the rotatable disk 8. The powdered materials 2 are fluidized by air 10 supplied through inlets 12 located under the rotatable disk 8. The air 10 flows upward and out of the vessel through exhaust outlet 14. The air 10 supplied to the vessel 1 is transported to the inlet 12 through conduit means 16. The conduit means 16 is in thermal communication with heat exchanging means 18. The heat exchanger provides temperature control for the air 10. The heat exchanger may utilize a variety of common heat transferring means such as a steam jacket, oil jacket, or radiant heat source. The air 10 may be filtered after passing through the zone of the conduit means in thermal communications with the heat exchanger by passing the air through a filter means 30. The air flow through the vessel may be affected by a fan or turbine 24 mechanically linked 25 such as by a shaft to a means for providing torque 27 such as a variable speed motor disposed with a primary filter 26 at the air intake 19. In an alternate embodiment the fan or turbine 32 mechanically linked 33 such as by a shaft to a means for providing torque 34 such as a variable speed motor could be disposed at the exhaust outlet 14.

EXAMPLE 1

This example describes a method for performing a partial melt granulation. The granules formed by this process appear to have the higher melting point materials adhering to the surface of the lower melting point particles.

| Ingredient No. | | % (W/W) | g//batch |
|---|---|---|---|
| I | d-pseudoephedrine HCl USP | 73.0 | 3,650 |
| II | Polyethylene glycol 8000 NF | 25.0 | 1,250 |
| III | Colloidal silicon dioxide NF | 1.0 | 50 |
| IV | Magnesium stearate NF | 1.0 | 50 |

Ingredients I, III and IV were admixed and then passed through a Fitzpatrick Comminutor Model D, knives forward, medium speed, #2AA screen. The milled material was then admixed with ingredient II and then added to the product container of a Glatt GPCG 5 rotor insert. The unit was hydraulically pressed. The supply air temperature controller was adjusted to about 10–12 degrees above the melting point of the binder material. The powders were then fluidized and the air flow adjusted by using the slit and exhaust air flap until the differential pressure across the rotor plate of approximately 150 mm of water was attained. The rotor was then turned on and the rotational speed was increased to 500 RPM. The exhaust air flow control flap and slit width were adjusted to attain an air flow that maintained proper fluidization. The bed was heated until a product bed temperature equal to 60° C. was obtained. The particle size of the granules formed by rotomelt granulation was determined after the granules were passed through a 14 mesh sieve using U.S. Standard Mesh.

| Particle size data: | Mesh Number | Weight Percent Retained |
|---|---|---|
| | 40 | 0.65 |
| | 60 | 18.33 |
| | 80 | 25.26 |
| | 100 | 12.16 |
| | 170 | 34.24 |
| | 270 | 2.81 |
| | Pan | 6.55 |

EXAMPLE 2

| Ingredient No. | | % (W/W) | g/batch |
|---|---|---|---|
| I | d-pseudoephedrine HCl USP | 48 | 2,400 |
| II | Colloidal silicon dioxide NF | 1 | 50 |
| III | Magnesium stearate NF | 1 | 50 |
| IV | Carnauba Wax NF | 50 | 2,500 |

The protocol employed in Example 1 was followed in this example except the product bed temperature was increased to 78° C. so that agglomeration would occur and ingredient II was omitted. The particle size of the granules formed by rotomelt granulation was determined after the granules were passed through a 14 mesh sieve.

| Mesh Number | Weight Percent Retained |
|---|---|
| 20 | 0.00 |
| 30 | 0.80 |
| 40 | 3.80 |
| 50 | 42.00 |
| 60 | 14.40 |
| 80 | 25.20 |

| Mesh Number | Weight Percent Retained |
| --- | --- |
| PAN | 13.80 |

EXAMPLE 3

| Ingredient No. | | % (W/W) | g/batch |
| --- | --- | --- | --- |
| I | Ibuprofen USP | 30 | 3,000 |
| II | Croscarmellose Sodium NF | 68 | 6,800 |
| III | Sodium Lauryl Sulfate NF | 2 | 200 |

The protocol employed in Example 1 was followed in this example except the product bed temperature was increased to 72° C. so that agglomeration would occur. The particle size of the granules was determined after the granules were passed through a 14 mesh sieve.

| Particle size data: | Mesh Number | Weight Percent Retained |
| --- | --- | --- |
| | 20 | 0.5 |
| | 30 | 2.0 |
| | 40 | 12.8 |
| | 50 | 61.4 |
| | 60 | 14.5 |
| | 80 | 8.5 |
| | Pan | 0.0 |

The granules formed by this process with ibuprofen have a narrow size distribution.

EXAMPLE 4

| Ingredient No. | | % (W/W) | g/batch |
| --- | --- | --- | --- |
| I | Ibuprofen USP | 50 | 5,000 |
| II | Croscarmellose Sodium NF | 50 | 5,000 |

The protocol employed in Example 3 was followed in this Example. The particle size of the granules were determined after the granules formed by rotomelt granulation were passed through a 14 mesh sieve.

| Particle Size Data: | Mesh Number | Weight Percent Retained |
| --- | --- | --- |
| | 20 | 1.49 |
| | 30 | 7.53 |
| | 40 | 50.55 |
| | 50 | 35.28 |
| | 60 | 4.06 |
| | 80 | 0.99 |
| | Pan | 0.10 |

Again as previously demonstrated the granules formed using ibuprofen as a binder have a very narrow size distribution.

We claim:

1. A process for producing granules by rotomelt granulation comprising mixing at least one powdered pharmaceutically active material and a powdered excipient material with a higher melting point than said powdered pharmaceutically active material, in a zone wherein both powdered materials are maintained in a fluidized state by contacting said powdered materials with a rising stream of gas in an apparatus having a rapidly rotating horizontal-disk located within a vessel having a bottom surface and said rapidly rotating disk is located on the bottom surface of the vertical vessel wherein the gas is at a temperature sufficient to cause the powdered pharmaceutically active material to at least partially melt thereby causing said powdered pharmaceutically active material to aggregate with said powdered excipient material to form granules which are spherical.

2. The process of claim 1 wherein the powdered pharmaceutically active material is selected from the group consisting gemfibrozil, guaifenesin, ibuprofen, isosorbide dinitrate, flurbiprofen and ketoprofen.

3. The process of claim 1 wherein the powdered pharmaceutically active material is ibuprofen.

4. The process of claim 1 herein the excipient is selected from the group consisting of fillers, disintegrants, lubricants, glidants and antiadherents.

5. The process of claim 2 wherein the amount of powdered pharmaceutically active material present is in the range of from about 10 weight percent to about 80 weight percent of the powdered materials based on the total amount of powdered material equaling 100 weight percent.

6. The process of claim 5 wherein additionally there is present a powdered dissolution enhancer selected from the group consisting of sodium carbonate, potassium carbonate and sodium bicarbonate.

7. The process of claim 1 wherein the powdered pharmaceutical active is ibuprofen and the amount of ibuprofen present is in the range of from about 20 to about 80 weight percent and the powdered excipient is selected from the group consisting of corn starch, maize starch, waxy maize starch, potato starch, rice starches, carboxymethyl starches, sodium starch glycolate, purified wood cellulose, carboxy cellulose, carboxymethyl cellulose, crosslinked carboxymethyl cellulose, low substituted hydroxypropyl cellulose, microcrystalline cellulose, combinations of sodium carboxymethyl cellulose and microcrystalline cellulose, alginic acid, guar gum, pectins, cation exchange resins, crosslinked homopolymers of vinylpyrrolidone, magnesium silicates, aluminium silicates, colloidal silicon, sucrose, dextrose, maltodextrins, lactose, fructose and combination of two or more thereof and the amount of powdered excipient present is in the range of from about 80 to about 20 weight percent wherein the weight percent is based on the total amount of the powdered materials equalling 100 weight percent.

8. The process of claim 1 wherein the powdered pharmaceutical active is ibuprofen and the amount of ibuprofen present is in the range of from about 10 to about 60 weight percent and the powdered excipient is selected from the group consisting of corn starch, maize starch, waxy maize starch, potato starch, rice starch, carboxymethyl starches, sodium starch glycolate, purified wood cellulose, carboxy cellulose, carboxymethyl cellulose, crosslinked carboxymethyl cellulose, low substituted hydroxypropyl cellulose, microcrystalline cellulose, combinations of sodium carboxymethyl cellulose and microcrystalline cellulose, alginic acid, guar gum, pectins, cation exchange resins, crosslinked homopolymers of vinylpyrrolidone, magnesium silicates, aluminium silicates, colloidal silicon, sucrose, dextrose, maltodextrins, lactose, fructose and combination of two or more thereof and the amount of powdered excipient present is in the range of from about 20 to about 40 weight percent and additionally there is present a powdered dissolution enhancer selected from the group consisting of sodium carbonate, potassium carbonate and sodium bicarbonate and the amount of powdered dissolution enhancer present is in the range of from about 20 to about 70 weight percent wherein the weight percent is based on the total amount of the powdered materials equalling 100 weight percent.

9. The process of claim 7 wherein the gas contacted with the powdered pharmaceutically active material and powdered excipient material is maintained at a temperature in the range of from about 68° C. to about 76° C.

10. A process for producing granules by rotomelt granulation comprising mixing a powdered binder material and a powdered pharmaceutically active material with a higher melting point than said powdered binder material in a zone wherein both powdered materials are maintained in a fluidized state by a rising stream of gas in an apparatus having a rapidly rotating horizontal-disk located within a vertical vessel having a bottom surface and said rapidly rotating disk is located on the bottom surface of the vertical vessel wherein said gas is at a temperature sufficient to cause the powdered binder material to at least partially melt thereby causing said powdered materials to aggregate and form granules.

11. The process of claim 10 wherein the binder is present in an amount in the range of from about 10 weight percent to about 80 weight percent and the powdered pharmaceutical active material is present in amount in the range of from about 20 to about 90 weight percent based on the total amount of powdered materials equalling 100 weight percent.

12. The process of claim 11 wherein optionally there is present one or more excipients or dissolution enhancers.

13. The process of claim 10 wherein the binder is selected from the group consisting of polyethylene glycol 4000, polyethylene glycol 6000, stearic acid, glyceryl monostearate, hydrogenated tallow, myristyl alcohol, myristic acid, stearyl alcohol, substituted monoglycerides, substituted diglycerides, substituted triglycerides, white beeswax, carnauba wax, castor wax, japan wax, acetylate monoglycerides, stearic acid and combinations of two or more thereof.

14. The process of claim 10 wherein the powdered pharmaceutical active is selected from the group consisting of terfenadine, chlorpheniramine maleate, clemastine fumarate, carbinoxamine maleate, promethazine hydrochloride, diphenhydramine, aspirin, salicylamide, ethanzamide, acetaminophen, diclofenac d-pseudoephedrine, dextromethorphan hydrobromide, dihydrocodeine phosphate, cloperastine hydrochloride, phenylpropanolamine hydrochloride, methylephedrine, potassium cresol sulfonate, morphine sulfate, codeine phosphate, belladonna alkaloids, pirenzepine, cimetidine, ranitidine, famotidine, pindolol, propranorol, alprenolol, oxprenolol, diltiazem, 5-fluorouracil, cephalexin, cefaclor, cinoxacin, enoxacin, ofloaxacin and pharmaceutically acceptable salts thereof.

* * * * *